United States Patent [19]

Taniguchi et al.

[11] 4,329,517
[45] May 11, 1982

[54] PROCESS FOR PRODUCTION OF MONO- OR DI-ORTHO-METHYL-SUBSTITUTED PHENOLS BY CATALYTIC METHYLATION AND CATALYST THEREFOR

[75] Inventors: Katsuo Taniguchi, Iwakuni; Kazunori Takahata; Yoshiaki An-Nen, both of Ohtake, all of Japan

[73] Assignee: Mitsui Petrochemical Industries Ltd., Tokyo, Japan

[21] Appl. No.: 149,583

[22] Filed: May 14, 1980

[30] Foreign Application Priority Data

| | | | |
|---|---|---|---|
| May 16, 1979 | [JP] | Japan | 54-59078 |
| Sep. 14, 1979 | [JP] | Japan | 54-117229 |
| Oct. 12, 1979 | [JP] | Japan | 54-130912 |
| Oct. 29, 1979 | [JP] | Japan | 54-138705 |
| Nov. 6, 1979 | [JP] | Japan | 54-142789 |
| Nov. 6, 1979 | [JP] | Japan | 54-142790 |
| Nov. 7, 1979 | [JP] | Japan | 54-143335 |

[51] Int. Cl.$^3$ .............................. C07C 37/11
[52] U.S. Cl. ...................... 568/804; 568/794; 252/447; 252/463; 252/472
[58] Field of Search ............... 568/804, 794, 472, 463; 252/447, 474, 463, 472

[56] References Cited

U.S. PATENT DOCUMENTS

| | | | |
|---|---|---|---|
| 3,716,589 | 2/1973 | Kotanigawa et al. | 568/804 |
| 3,855,318 | 12/1974 | Nakajima et al. | 568/804 |
| 3,953,529 | 4/1976 | Yonemitsu et al. | 568/804 |
| 4,208,537 | 6/1980 | Kawamata et al. | 568/804 |
| 4,227,024 | 10/1980 | Leach | 568/804 |

FOREIGN PATENT DOCUMENTS

| | | | |
|---|---|---|---|
| 39-6894 | 5/1964 | Japan . | |
| 47-7020 | 2/1972 | Japan . | |
| 47-37944 | 9/1972 | Japan . | |
| 47-38936 | 12/1972 | Japan . | |
| 49-13128 | 2/1974 | Japan | 568/804 |
| 50-5696 | 6/1975 | Japan . | |
| 50-76032 | 6/1975 | Japan . | |
| 51-11101 | 4/1976 | Japan . | |
| 51-12610 | 4/1976 | Japan . | |
| 53-90229 | 8/1978 | Japan . | |
| 53-101318 | 9/1978 | Japan . | |
| 1421257 | 1/1976 | United Kingdom | 568/804 |

*Primary Examiner*—Werren B. Lone
*Attorney, Agent, or Firm*—Sherman & Shalloway

[57] ABSTRACT

In a process for producing a mono- or di-ortho-methyl-substituted phenol which comprises methylating a phenol having one or two ortho-hydrogens with methanol in the presence of a catalytic amount of a catalyst comprising a major proportion of an oxide of iron as a first component (A) and a minor proportion of at least one oxide of metal other than iron as a second component (B), the improvement wherein said metal other than iron in component (B) is a metal selected from the group consisting of Ga, Ge, Y, Nb, Hf, Bi and Ta; and a catalyst used therefor.

5 Claims, No Drawings

PROCESS FOR PRODUCTION OF MONO- OR DI-ORTHO-METHYL-SUBSTITUTED PHENOLS BY CATALYTIC METHYLATION AND CATALYST THEREFOR

This invention relates to a process for the production of mono- or di-ortho-methyl-substituted phenols such as 2,6-xylenol and ortho-methyl phenol (i.e., o-cresol), by catalytic methylation of phenols having one or two ortho-hydrogens, such as phenol, ortho-, meta- and para-cresols, with methanol in the presence of a catalytic amount of a catalyst.

More specifically, this invention relates to an improved process which exhibits an improved selectivity for ortho-methylation (denoting the total selectivities for 2-, 6- and 2,6-methylations) and an improved selectivity for 2,6-methylation while effectively inhibiting the undesirable decomposition of methanol. In particular, the present invention pertains, in a process for producing mono- or di-ortho-methyl-substituted phenols by catalytic methylation of phenols having one or two ortho-hydrogens with methanol in the presence of a catalytic amount of a catalyst comprising a major proportion of an oxide of iron as a first component (A) and a minor proportion of at least one oxide of a metal other than iron as a second component (B), the improvement wherein said metal other than iron is a metal selected from the group consisting of gallium (Ga), germanium (Ge), yttrium (Y), niobium (Nb), hafnium (Hf), bismuth (Bi) and tantalum (Ta).

The mono- or di-ortho-methyl-substituted phenols are useful as intermediates for the production of various chemicals. For example, 2,6-xylenol is useful as a material for the production of polyphenylene oxide resins. Many suggestions have been made in the past for the production of such phenols having one or two methyl groups at the ortho-position by the catalytic methylation of phenols having one or two ortho-hydrogens with methanol in the presence of a catalytic amount of a catalyst comprising a major proportion of an oxide of iron as a first component (A) and a minor proportion of at least one oxide of a metal other than iron as a second component (B).

Known catalysts for the aforesaid catalytic methylation include magnesium oxide (Japanese Patent Publication No. 6894/67), manganese oxide (Japanese Patent Publication No. 11101/76), and iron oxide (British Pat. No. 717,588 corresponding to Japanese Patent Publication No. 47446/77).

These prior art methods using the known oxides of metals have their own technical defects. For example, in a method involving using a magnesium oxide catalyst, the selectivity for ortho-methylation is good, but the use of higher temperatures in an attempt to increase the activity of the catalyst results in shortening of the active lifetime of the catalyst. Moreover, the magnesium oxide catalyst lends itself to inconvenient handling because it is apt to be powderized during storage and transportation. A method involving using the iron oxide catalyst have the advantage that it shows high activity at lower temperatures than those used for the magnesium oxide catalyst. But it has the defect that the selectivity for ortho-methylation is insufficient, and undersirable decomposition of methanol tends to occur vigorously. A method involving using the manganese oxide catalyst has the defect that the catalyst life is short, large amounts of high-boiling by-products such as 2,4,6-trimethylphenol are formed, and decomposition of methanol is liable to take place vigorously.

In an attempt to remove the defects associated with the use of these catalysts comprising a single component of an oxide of a metal, various suggestions have been made heretofore in which to use catalysts composed of an oxide of iron and at least one oxide of a metal other than iron.

For example, known suggested methods of this type include the use of a composite catalyst of a ferrite having the formula $MFe_2O_4$ wherein M is Zn, Mg, Ca, Ba, Co, Ni, Cr, Mn, Cd, Cu, Ag, Cu-Zn and Ag-Zn (U.S. Pat. No. 3,716,589; Japanese Patent Publication No. 37812/71); a vanadium oxide catalyst which may additionally contain iron oxide and at least one other oxide of Mg, Ti, Mn, Be or B (U.S. Pat. No. 3,855,318; Japanese Patent Publications Nos. 37943/72, 37945/72 and 37946/72); an iron oxide catalyst which contains Fe in an atomic ratio of 9–1/9 (Japanese Patent Publication No. 37944/72); a catalyst component of the iron oxide-zinc oxide-chromium oxide type or the iron oxide-titanium oxide type (Japanese Patent Publication No. 7020/72); a catalyst comprised of oxides of U and Fe in which the atomic ratio of Fe to U is from 9 to 1/9 (Japanese Patent Publication No. 5696/75); a catalyst composed of a sintered mixture of ferric oxide, at least one divalent metal oxide of the general formula MO wherein M is selected from Zn, Mg, Co, Ni, Cr and Cd and a small amount of manganese oxide calculated in terms of Mn, up to about 1.0% by weight of the ferric and divalent metal oxides (U.S. Pat. No. 3,923,907; Japanese Patent Publication No. 10023/76); a catalyst comprised of oxides of Cr and Fe in which the Fe:Cr atomic ratio is from 9 to 1/9 (Japanese Patent Publication No. 12610/76); a catalyst selected from the group consisting of (a) a mixture of iron oxide and silica in which the atomic ratio of Fe to Si is 100: 0.03–200 and (b) a mixture of iron oxide and chromium oxide in which the atomic ratio of Fe to Si to Cr is 100:0.1–5:0-.1–5 (U.S. Pat. No. 3,953,529; Japanese Patent Publications Nos. 12689/77 and 12690/77); a catalyst containing iron oxide, silica, chromium oxide and one or more alkali metal compound (U.S. Pat. No. 4,024,195; Japanese Patent Publication No. 12692/77); a catalyst composed of iron oxide and an oxide of a metal selected from the group consisting of Mg, Cr and Al (Japanese Laid-Open Patent Publication No. 38936/72); a catalyst composed mainly of iron oxide and zinc oxide with the reaction being carried out in the copresence of carbon dioxide gas and/or hydrogen sulfide (Japanese Laid-Open Patent Publication No. 76032/75); a catalyst composed of iron oxide and antimony oxide or boron oxide (Japanese Laid-Open Patent Publication No. 90229/78); and a catalyst composed of iron oxide, boron oxide, chromium oxide and an alkali metal compound (Japanese Laid-Open Patent Publication No. 101318/78).

These prior suggestions are still unable to provide an improved process which can attain satisfactory selectivities for ortho-methylation and 2,6-methylation and inhibit effectively the undesirable decomposition of methanol while achieving various improvements such as the ease of catalyst preparation, superior catalytic activity, long catalyst lives and good producibility of reaction. It has been strongly desired to develop such a process.

In order to meet this desire, the present inventors made extensive investigations. These investigations have led to the discovery that by combining at least one metal selected from the group consisting of Ga, Ge, Y, Nb, Hf, Bi and Ta not suggested in the prior methods with an oxide of iron, there can be provided an improved catalyst which shows high catalytic activity and satisfactory selectivities for ortho-methylation and 2,6-methylation while markedly inhibiting the undesirable decomposition of methanol, and provides various improvements such as the ease of catalyst preparation, a long catalyst life, the reproducibility of the reaction, and the economically feasible cost of production.

It is an object of this invention therefore to provide an improved process for producing mono- or di-ortho-methyl substituted phenols by the catalytic methylation of phenols having one or two ortho-hydrogens.

Another object of this invention is to provide an improved process for use in the practice of the aforesaid process.

The above and other objects of this invention will become more apparent from the following description.

The catalyst used in the process of this invention comprises a major proportion of an oxide of iron as a first component (A) and a minor proportion of at least one oxide of a metal other than iron, as a second component (B), the other metal being selected from the group consisting of Ga, Ge, Y, Nb, Hf, Bi and Ta. The catalyst may further contain, as a third component (C) at least one component selected from the group consisting of (C-1) an oxide of a metal selected from Mg, Zn, Al, Si, Cr, Mo, W, Sn and Zr, (C-2) a basic alkali metal compound of a metal selected from K, Na and Li, and (C-3) carbon.

Examples of the oxide of iron as a first component (A) are iron (II) oxide, iron (III) oxide and a mixture of these. Of these, the use of iron (III) oxide or a mixture of iron (III) oxide and iron (II) oxide is preferred. The first component (A) may be prepared by calcining a ferrous compound, a ferric compound or a mixture of these (such as the nitrate, sulfate, phosphates, borates, fluorides, chlorides, bromides, iodides, perchlorates, formates, acetates, propionates, benzoates, oxalates and hydroxides.) These oxides of iron may be used in a combination with each other.

Examples of the oxide of metal as the second component (B) include gallium oxides such as gallous oxide, gallic oxide or a mixture of these; germanium oxides such as germanous oxide, germanic oxide or a mixture of these; yttrium oxides such as diyttrium trioxide; niobium oxides in various oxidation states, such as niobium monoxide, diniobium trioxide, niobium dioxide, diniobium pentoxide, or mixtures of these; hafnium oxides such as hafnium dioxide; tantalum oxides such as tantalum dioxide, ditantalum pentoxide, or mixtures of these; and bismuth oxides in the various oxidation states, such as bismuth monoxide, bismuth trioxide, bismuth pentoxide, or mixtures of these.

These oxides of metals as the second component (B) may be used singly or as mixtures of two or more.

At least one oxide of a metal selected from the group consisting of Ga, Ge and Hf is preferred as the second component (B). The oxide of metal as the second component (B) can be produced by calcining a compound of at least one metal selected from the group consisting of Ga, Ge, Y, Nb, Hf, Ta and Bi.

The catalyst used in this invention may further contain the third component (C) described hereinabove in addition to the first component (A) and the second component (B). The third component (C) may be at least one component selected from component (C-1) which is an oxide of a metal selected from the group consisting of Mg, Zn, Al, Si, Cr, Sn, Mo, W and Zr, component (C-2) which is a basic alkali metal compound of a metal selected from the group consisting of K, Na and Li, and component (C-3) which is carbon.

Examples of the component (C-1) are magnesia, zinc suboxide, zinc oxide, a mixture of zinc oxide and zinc suboxide, aluminas such as alpha-alumina, beta-alumina, gamma-alumina and mixtures of these, oxides of silicon such as silica gel, silica sol and alumina-silica gel, oxides of chromium such as chromium monoxide, dichromium trioxide, chromium dioxide, dichromium pentoxide, chromium trioxide and mixtures of these, oxides of molybdenum such as molybdenum monoxide, dimolybdenum trioxide, molybdenum dioxide, dimolybdenum pentoxide, molybdenum trioxide and mixture of these, oxides of tungsten such as tungsten dioxide, ditungsten pentoxide, tungsten trioxide and mixtures of these, oxides of tin such as stannous oxide stannic oxide, and mixtures of these, and zirconia. These oxides as the component (C-1) may be used singly or as mixtures. Of these, magnesia, alumina and dichromium trioxide are especially preferred.

Examples of the component (C-2) include basic alkali metal compounds such as the oxides, hydroxides, carbonates, phosphates and borates of Na, K and Li, preferably Na and K; and basic organic alkali metal compounds such as the methoxides, ethoxides, propoxides, formates, acetates, propionates, benzoates, phenolates, cresolates and xylenolates of the aforesaid alkali metals.

Of these compounds as the component (C-2), the basic inorganic alkali metal compounds are preferred. The oxides, hydroxides and carbonates are especially preferred.

Examples of the carbon as component (C-3) are graphite and activated carbon, the former being preferred.

The catalyst used in this invention may be in any desired form. For example, it may be a shaped mixture obtained by molding a mixture of the components (A), (B) and optionally (C) into a desired form such as granules, pellets, spheres, extruded articles and powder using a suitable binder, or a supported catalyst obtained by supporting these components on a suitable carrier such as diatomaceous earth, silica gel, alumina, titatia and pumice.

Examples of the binder used to prepare the molded catalyst are clay, potter's clay, cement and gypsum.

The catalyst of this invention may be prepared by procedures known per se. For example, it may be prepared by mixing the first and second components (A) and (B) optionally together with the third component (C); or molding the resulting mixture into a desired form with or without the aforesaid binder; or calcining metal compounds capable of forming the oxides as the components (A) and (B) and optionally the component (C) in the absence of a carrier or after impregnating them in a carrier.

According to a preferred embodiment of this invention, at least one of the first component (A) and the second component (B) is derived from a compound in the colloidal state. The catalyst so prepared has good catalytic activity, a long active lifetime and exhibits a high selectivity both for ortho-methylation and 2,6-methylation and can effectively inhibit the undesirable decomposition of methanol.

The first component (A) is in the form of an oxide of Fe (II) and/or Fe (III). Or compounds capable of being converted to oxides during catalyst preparation such as by calcination may be used. Examples of the iron compounds other than oxides are ferrous or ferric nitrate, sulfate, phosphate, borate, fluoride, chloride, bromide, iodide, perchlorate, formate, acetate, propionate, benzoate, oxalate, and hydroxide.

Of these iron compounds, water-soluble iron compounds are preferred. Especially preferred are iron hydroxides and iron oxides and mixtures of these whose main component is non-crystalline and colloidal (e.g., sol- or gel-like).

The second component (B) is an oxide of a metal selected from the group consisting of Ga, Ge, Y, Nb, Hf, Bi and Ta. Other compounds of these metals which can be converted to these oxides during catalyst preparation such as by calcination may be used. Examples of the other metal compounds capable of being converted to the oxides include the halides, nitrates, sulfates, perchlorates, phosphates, borates, hydroxides, oxygenates, alkoxides, formates, acetates, propionates, benzoates, phenolates, cresolates and xylenolates of these metals. Those which are soluble in water and/or organic solvents are preferred. Examples of the organic solvents are alcohols, ethers, and aliphatic carboxylic acids. The concentration of the aforesaid metal compound in the solution is optional. Preferred metal compound solutions are aqueous solutions, alcohol solutions, ether solutions and aliphatic carboxylic acid solutions of these metal compounds. The aqueous solutions are especially preferred.

In the aforesaid preferred embodiment of this invention in which one or both of the first component (A) and the second component (B) are derived from a compound in the colloidal state, the compound in the colloidal state may be prepared by various known procedures. For example, it may be prepared by the action of a base such as an aqueous solution of sodium hydroxide or ammonia on a solution of a relatively stable iron compound such as a sulfate, nitrate, phosphate or borate of iron. By removing the medium from the sol-like iron compound so prepared, a gel-like iron compound results. The sol-like iron compounds are preferred among the colloidal iron compounds for use in the preparation of the catalyst of this invention.

When a compound of a metal selected from the group consisting of Ga, Ge, Y, Nb, Hf, Bi and Ta in the colloidal state is used in accordance with the aforesaid preferred embodiment, the compound may be prepared by known procedures.

The colloidal metal compound may be a sol-like compound or gel-like compound of the aforesaid metals. As the colloidal metal compound, the use of a colloidal metal compound of at least one metal selected from Ga, Ge and Hf is preferred. Germanium compounds in the colloidal state are especially preferred.

The metal compound in colloidal state can be prepared by contacting a relatively unstable metal compound such as a halide or alkoxide of the aforesaid metal with water, or contacting a solution of such a metal compound in an organic solvent such as an alcohol (e.g., methanol, ethanol or isopropanol) or a ketone (e.g., acetone) with water with stirring to decompose the metal compound. Or it may also be prepared by the action of a base such as an aqueous solution of sodium hydroxide or ammonia on a solution of a relatively stable metal compound such as a sulfate, nitrate, phosphate or borate of the aforesaid metal. By removing the medium from the sol-like metal compound so prepared, a gel-like compound of the aforesaid metal can be obtained. Among the aforesaid colloidal metal compounds, the sol-like metal compounds are preferred for use in the preparation of the catalyst of this invention.

According to this preferred embodiment, the catalyst of this invention can be prepared by calcining a solid mixture obtaining from a dispersed mixture which is in such a combination as (1) a compound of iron in colloidal state which can be prepared as above, and the second component (B) or a compound convertible to the second component (B) by calcination with or without the third component (C) and/or a compound capable of forming the component (C) by calcination; (2) the first component (A) or a compound convertible to the first component (A) by calcination, a compound of a metal in (B) component in colloidal state which can be prepared as above, and optionally the third component (C) and/or a compound capable of forming the third component (C) by calcination; or (3) the compound of iron in colloidal state, the compound of a metal in (B) component in colloidal state and optionally the third component (C) and/or a compound capable of forming the third component (C) by calcination. The aforesaid mixed dispersed mixture can be prepared by adding the individual components to water or an organic medium such as an alcohol (e.g., methanol, ethanol or isopropanol) or a ketone (e.g., acetone) and mixing them with stirring. If at this time, either one of the first component (A) or the compound convertible thereto and the second component (B) or the compound convertible thereto contains a sufficient amount of water or the organic medium, there is no need to use an additional supply of water or the organic solvent. When it is desired to form a carrier-supported catalyst, a carrier of the type exemplified hereinabove may be added to the mix-dispersed mixture. Furthermore, this dispersed mixture may further contain a suitable binder such as clay, potter's clay, cement and gypsum.

Removal of the medium from the resulting dispersed mixture gives a solid mixture. Usually, the solid mixture can be obtained by drying the dispersed mixture by, for example, distilling off the medium.

When a carrier-supported catalyst in accordance with this invention is to be prepared, or a binder is to be incorporated in the catalyst of this invention, or the third component (C) is to be added to the catalyst of this invention, it is also possible to add the carrier, the binder or the third component (C) or a metal compound convertible thereto to the solid mixture obtained by the above procedure instead of incorporating the carrier, the binder or the third component (C) or a metal compound convertible thereto during the formation of the aforesaid dispersed mixture.

The catalyst used in this invention can be obtained by calcining the solid mixture prepared by the aforesaid procedures. In calcination, the solid mixture may be in the form of a powder or a molded article such as spheres, pellets or lumps. The calcination temperature is, for example, about 300° to about 900° C., preferably about 400° to about 600° C. The calcination can be carried out in the presence of a molecular oxygen-containing gas such as air, or in an atmosphere of an inert gas such as nitrogen gas. Calcination in the presence of a molecular oxygen-containing gas is preferred because it gives a catalyst which is highly active and selective for ortho-methylation.

The catalyst of this invention comprises a major proportion of an oxide of iron as a first component (A) and a minor proportion of an oxide of a metal selected from the group consisting of Ga, Ge, Y, Nb, Hf, Bi and Ta as a second component (B). Per gram-atom of iron in the first component (A), the amount of the second component (B), calculated as metal, is preferably about 0.003 to about 0.3 gram-atom, more preferably about 0.005 to about 0.15 gram-atom, and the amount of the third component (C), calculated as metal or carbon, is preferably about 0.0001 to about 0.1 gram-atom, more preferably about 0.001 to about 0.05 gram-atom. The amounts of the individual compounds used in catalyst preparation may be similar to these amounts in the final catalyst.

According to the process of this invention, a phenol having one or two ortho-hydrogens is methylated with methanol in the presence of the aforesaid catalyst composed of the first component (A), the second component (B) and optionally the third component (C).

The starting phenol may include phenols having the following formula

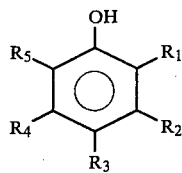

(1)

wherein each of $R_1$, $R_2$, $R_3$, $R_4$ and $R_5$ represents a member selected from the group consisting of hydrogen, lower alkyl such as $C_1$–$C_4$ alkyl, cycloalkyl such as cyclohexyl and aryl such as phenyl, provided that one or both of $R_1$ and $R_5$ are hydrogen atoms.

Examples of the lower alkyl groups are methyl, ethyl, n-, iso-, and tert-propyl, and n-, iso-, tert-, and sec-butyl.

Specific examples of the phenols include phenol; cresols such as o-cresol, m-cresol and p-cresol; xylenols such as 2,3-xylenol, 2,4-xylenol, 2,5-xylenol and 3,5-xylenol; trimethylphenols such as 2,3,4-trimethylphenol, 2,3,5-trimethylphenol and 3,4,5-trimethylphenol; and 2,3,4,5-tetramethylphenol. Of these phenols, phenol and cresols, particularly o-cresol, are preferred.

The reaction in accordance with this invention can be performed both in the liquid phase and the vapor phase, but the vapor phase reaction is preferred.

When the reaction is to be carried out in the vapor phase, the reaction temperature is preferably about 250° to about 450° C., more preferably about 300° to about 400° C. In the reaction, the catalyst may be used as a fixed bed or a fluidized bed. When the reaction is carried out in a fixed catalyst bed, the liquid hourly space velocity (LHSV) of the starting material is preferably 0.1 to 10 hr$^{-1}$, more preferably 0.5 to 5 hr$^{-1}$. The reaction may be carried out at reduced or elevated pressures, preferably at a pressure of about 1 to about 30 kg/cm$^2$.G. The unreacted methanol is separated from the reaction mixture after the reaction, and the residue is treated in a customary manner by distillation, crystallization, extraction, etc. to obtain the desired ortho-methylated phenol. The recovered unreacted methanol and phenol having ortho-hydrogen are recycled to the reaction system for re-use. The presence of water or steam in the reaction system is preferred because it is conducive to the inhibition of localized heating in the system and also to the inhibition of methanol decomposition.

When the reaction is carried out in the liquid phase, the reaction temperature is preferably about 150° to about 400° C., more preferably about 200° to about 350° C., and the initial pressure of reaction is preferably about 5 to about 50 kg/cm$^2$-gauge. The reaction can be performed either batchwise or continuously.

The following Examples specifically illustrate the process of this invention. The various measured values in these examples are defined as follows:

(1) Conversion (%) of phenol $$\frac{\left(\begin{array}{c}\text{Amount (moles) of}\\ \text{phenol fed}\end{array}\right) - \left(\begin{array}{c}\text{Amount (moles) of}\\ \text{unreacted phenol}\end{array}\right)}{\text{Amount (moles) of phenol fed}} \times 100$$

(2) Selectivity (%) for each product $$\frac{\text{Amount (moles) of each product formed}}{\left(\begin{array}{c}\text{Amount (moles)}\\ \text{of phenol fed}\end{array}\right) - \left(\begin{array}{c}\text{Amount (moles) of}\\ \text{unreacted phenol}\end{array}\right)} \times 100$$

(3) Selectivity (%) for ortho-methylation $$\begin{array}{c}\text{Selectivity}\\ \text{for 2,6-xylenol}\end{array} + \begin{array}{c}\text{Selectivity}\\ \text{for o-cresol}\end{array}$$

(4) Ratio of decomposition of methanol (%)

$$1 - \frac{\left(\begin{array}{c}\text{Amount (moles)}\\ \text{of o-cresol}\\ \text{formed}\end{array}\right) + \left(\begin{array}{c}\text{Amount (moles)}\\ \text{of 2,6-xylenol}\\ \text{formed}\end{array}\right) \times 2}{\left(\begin{array}{c}\text{Amount (moles)}\\ \text{of methanol}\\ \text{fed}\end{array}\right) - \left(\begin{array}{c}\text{Amount (moles)}\\ \text{of unreacted}\\ \text{methanol}\end{array}\right)} \times 100$$

EXAMPLES 1 TO 8

Ferric nitrate nonahydrate (202.0 g) was dissolved in 2 liters of distilled water, and 25% ammonia water was gradually added to adjust the pH of the solution to 7. The resulting precipitate was washed with water and collected by filtration. Then, 0.55 g of germanium dioxide was added, and the mixture was kneaded for 1 hour in an automatic mortar. The resulting mixture was dried for one day at 90° C., and then calcined at 450° C. for 3 hours to prepare a catalyst comprising iron oxide and germanium oxide. Atomic absorptiometric analysis of the catalyst showed that the iron:germanium atomic ratio in the catalyst was 99:1.

The catalyst was pulverized to a size of 6 to 10 mesh, and 20 ml of the pulverized catalyst was packed into a Pyrex reaction tube having an inside diameter of 20 mm and heated to 350° C. When this temperature was reached, a liquid mixture of methanol and phenol in a mole ratio of 5:1 was fed into the reaction tube at a rate of 14 ml/hr (LHSV=0.7 hr$^{-1}$) to react them. The results are shown in Table 1.

Catalysts comprising iron oxide-gallium oxide, iron oxide-bismuth oxide, iron oxide-yttrium oxide, iron oxide-niobium oxide, iron oxide-hafnium oxide, and iron oxide-tantalum oxide, respectively, were prepared in the same way as above except that in the catalyst preparation in Example 1 above, 0.55 g of germanium dioxide was changed respectively to 4.08 g of gallium nitrate octahydrate (Example 2), 7.50 g of bismuth nitrate pentahydrate (Example 3), 3.49 g of yttrium (III) oxide (Example 4), 2.71 g of niobium (V) oxide (Example 5), 2.14 g of hafnium (II) oxide (Example 6), and 6.83 g of tantalum (V) oxide (Example 7). Phenol was reacted in the same way as in Example 1 except that each of these catalysts was used. The results are also shown in Table 1.

A catalyst comprising iron oxide, germanium oxide and gallium oxide was prepared in the same way as in Example 1 except that the amount of the germanium dioxide was increased to 1.08 g, and 2.06 g of gallium nitrate octahydrate was further added. Phenol was reacted acted in the same way as in Example 1 using this catalyst The results are also shown in Table 1. (Example 8)

The data given in Table 1 were obtained at the end of 20 hours after the initiation of the reaction when the reaction was in the steady state.

COMPARATIVE EXAMPLES 1 TO 15

A catalyst was prepared from ferric nitrate nonahydrate alone in the same way as in Example 1 (Comparative Example).

Catalysts were also prepared in the same way as in Example 1 except that the germanium dioxide used in Example 1 was changed respectively to magnesium nitrate (Comparative Example 2), aluminum nitrate (Comparative Example 3), silica sol (Comparative Example 4), calcium nitrate (Comparative Example 5), zinc nitrate (Comparative Example 6), scanadium oxide (Comparative Example 7), ammonium meta-vanadate (Comparative Example 8), chromium nitrate (Comparative Example 9), indium nitrate (Comparative Example 10), tin nitrate (Comparative Example 11), zirconium nitrate (Comparative Example 12), antimony oxide (Comparative Example 13), ammonium molybdate (Comparative Example 14) and ammonium tungstate (Comparative Example 15). The results reaction as in Example 1 was performed using each of these catalysts. The results are also shown in Table 1.

washed with water and collected by filtration. Then, a colloidal (sol-like) germanium compound prepared by hydrolyzing 3.91 g of germanium tetraethoxide with aqueous ethanol was added to form a dispersed mixture. The mixture was kneaded for 1 hour in an automatic mortar. The resulting mixture was dried for one day at 90° C., and then calcined at 450° C. for 3 hours to afford a catalyst comprising iron oxide and germanium oxide.

The catalyst was pulverized to a size of 6 to 10 mesh, and 20 ml of the pulverized catalyst was packed into a Pyrex reaction tube having an inside diameter of 20 mm and heated to 355° C. After this temperature was reached, a mixture of phenol, methanol and $H_2O$ in a mole ratio of 1:5:2 was fed into the reaction tube at a rate of 25 ml/hr (LHSV = 1.25 $hr^{-1}$) to react them. The results are shown in Table 2.

An iron oxide-gallium oxide catalyst (Example 10), an iron oxide-niobium oxide catalyst (Example 11) and an iron oxide-tantalum oxide catalyst (Example 12) were prepared in the same way as in Example 9 except that the sol-like germanium compound was changed to a sol-like gallium compound obtained by gradually adding 25% ammonia water to an aqueous solution containing 6.20 g of gallium nitrate octahydrate (Example 10), a sol-like niobium compound obtained by hydrolyzing 4.19 g of niobium pentachloride (Example 11), and a sol-like tantalum compound obtained by hydrolyzing tantalum pentachloride (Example 12). The same reaction as in Example 9 was carried out except that each of these catalysts were used. The results are shown in Table 2.

EXAMPLES 13 AND 14

Ferric nitrate nonahydrate (202.0 g) was dissolved in 2 liters of distilled water, and 25% ammonia water was gradually added to adjust the pH of the solution to 7.

TABLE 1

| Example (Ex.) or Comparative Example (CEx.) | Catalyst (metal atom ratio) | Conversion of phenol (%) | Selectivity for o-cresol (%) | Selectivity for 2,6-xylenol (%) | Selectivity for 2,4,6-trimethyl phenol (%) | Selectivity for others (%) | Selectivity for o-methylation (%) | Ratio of decomposition of methanol (%) |
|---|---|---|---|---|---|---|---|---|
| Ex. 1 | Fe/Ge = 99/1 | " | 0.6 | 98.1 | 0.4 | 0.9 | 98.7 | 30.4 |
| Ex. 2 | Fe/Ga = 98/2 | 100 | 2.6 | 96.5 | 0.6 | 0.9 | 98.5 | 31.6 |
| Ex. 3 | Fe/Bi = 97/3 | 95.9 | 8.0 | 88.5 | 0.3 | 3.2 | 96.5 | 36.8 |
| Ex. 4 | Fe/Y = 97/3 | 94.8 | 14.3 | 82.0 | 0.8 | 2.9 | 96.3 | 33.8 |
| Ex. 5 | Fe/Nb = 98/2 | 99.0 | 6.0 | 90.2 | 0.9 | 2.9 | 96.2 | 36.4 |
| Ex. 6 | Fe/Hf = 98/2 | 98.0 | 8.9 | 90.0 | 0.8 | 0.3 | 98.9 | 32.4 |
| Ex. 7 | Fe/Ta = 98/2 | 97.2 | 11.5 | 85.5 | 0.6 | 2.4 | 97.0 | 38.3 |
| Ex. 8 | Fe/Ga/Ge = 97/1/2 | 100 | 3.6 | 95.2 | 0.6 | 0.6 | 98.8 | 31.2 |
| CEx. 1 | Fe | 90.0 | 37.7 | 50.3 | 1.5 | 10.5 | 88.0 | 62.0 |
| CEx. 2 | Fe/Mg = 97/3 | 92.5 | 40.5 | 56.8 | 0.4 | 2.3 | 97.3 | 60.0 |
| CEx. 3 | Fe/Al = 98.8/1.2 | 96.6 | 26.4 | 71.3 | 0.8 | 1.5 | 97.7 | 52.2 |
| CEx. 4 | Fe/Si = 98.8/1.2 | 98.2 | 21.0 | 77.2 | 0.4 | 1.4 | 98.2 | 56.1 |
| CEx. 5 | Fe/Ca = 99/1 | 83.1 | 59.3 | 37.3 | 0.6 | 2.8 | 96.6 | 63.4 |
| CEx. 6 | Fe/Zn = 97/3 | 80.4 | 47.2 | 49.8 | 0 | 3.0 | 97.0 | 65.0 |
| CEx. 7 | Fe/Sc = 97/3 | 86.2 | 57.0 | 40.6 | 0.8 | 1.6 | 97.6 | 58.3 |
| CEx. 8 | Fe/V = 97/3 | 91.6 | 28.5 | 68.3 | 1.4 | 1.8 | 96.8 | 61.4 |
| CEx. 9 | Fe/Cr = 98.8/1.2 | 97.6 | 26.4 | 70.6 | 0.8 | 2.2 | 97.0 | 62.1 |
| CEx. 10 | Fe/In = 97/3 | 98.1 | 33.0 | 65.0 | 1.2 | 0.8 | 98.0 | 54.8 |
| CEx. 11 | Fe/Sn = 95/5 | 91.6 | 30.7 | 66.1 | 0.3 | 2.9 | 96.8 | 36.8 |
| CEx. 12 | Fe/Zr = 96/4 | 92.2 | 32.9 | 65.0 | 0.5 | 1.6 | 97.7 | 32.0 |
| CEx. 13 | Fe/Sb = 97/3 | 50.5 | 68.3 | 27.7 | 1.0 | 3.0 | 96.0 | 60.2 |
| CEx. 14 | Fe/Mo = 97/3 | 96.0 | 23.7 | 73.2 | 0.4 | 2.7 | 96.9 | 37.2 |
| CEx. 15 | Fe/W = 98/2 | 90.5 | 43.2 | 54.3 | 0.8 | 1.7 | 97.5 | 42.2 |

EXAMPLES 9 TO 12

Ferric nitrate nonahydrate (202.0 g) was dissolved in 2 liters of distilled water, and 25% ammonia water was gradually added to adjust the pH of the solution to 7. The resulting amorphous sol-like iron hydroxide was washed with water and collected by filtration. It was then added to 2 liters of an aqueous solution containing 1.62 g of germanium dioxide. The mixture was thoroughly stirred to obtain a dispersed mixture containing the sol-like iron hydroxide. The water was removed by heating, and the mixture was dried at 90° C. for one day, and calcined at 450° C. for 3 hours to prepare a catalyst comprising iron oxide and germanium oxide.

The catalyst was pulverized to a size of 6 to 10 mesh, and 20 ml of the pulverized catalyst was packed into a Pyrex reaction tube having an inside diameter of 20 mm, and heated to 355° C. After this temperature was reached, a mixture of phenol, methanol and H₂O in a mole ratio of 1:5:2 was fed into the reaction tube at a rate of 30 ml/hr (LHSV=1.5 hr$^{-1}$) to react them. The results are shown in Table 2.

A catalyst comprising iron oxide and gallium oxide (Example 14) was prepared in the same way as in the catalyst preparation in Example 13 except that 2 liters of an aqueous solution containing 6.19 g of gallium nitrate octahydrate was used instead of 2 liters of the aqueous solution containing 1.62 g of germanium dioxide. The same reaction as in Example 1 was performed using the resulting catalyst. The results are shown in Table 2.

collected by filtration. Then, 0.97 g of germanium dioxide and 2.32 g of aluminum nitrate nonahydrate as a component for forming the third component (C) were added. The mixture was kneaded for 1 hour in an automatic mortar. The resulting mixture was dried for a day at 90° C., and then calcined at 450° C. for 3 hours to afford a ternary catalyst comprising iron oxide, germanium oxide and aluminum oxide. Atomic absorptiometric analysis of the resulting catalyst showed that the atomic ratio of Fe:Ge:Al in the catalyst was 97:1.8:1.2.

The catalyst was pulverized to a size of 6 to 10 mesh, and 20 ml of the pulverized catalyst was packed into a Pyrex reaction tube having an inside diameter of 20 mm and heated to 355° C. After this temperature was reached, a mixture of phenol, methanol and H₂O in a mole ratio of 1:5:2 was fed into the reaction tube at a rate of 14 ml/hr (LHSV=0.7 hr$^{-1}$) to react them. The results obtained at the end of 50 hours and 300 hours respectively after the initiation of the reaction are shown in Table 4.

EXAMPLES 26 TO 68

TABLE 2

| Example | Catalyst (metal atom ratio) | Conversion of phenol (%) | Selectivity for o-cresol (%) | Selectivity for 2,6-xylenol (%) | Selectivity for 2,4,6-trimethyl phenol (%) | Selectivity for others (%) | Selectivity for o-methylation (%) | Ratio of decomposition of methanol (%) |
|---|---|---|---|---|---|---|---|---|
| 9 | Fe/Ge = 97/3 | 100 | 5.1 | 93.2 | 0.9 | 0.8 | 98.3 | 30.0 |
| 10 | Fe/Ga = 97/3 | 100 | 7.3 | 91.4 | 0.4 | 0.9 | 98.7 | 30.7 |
| 11 | Fe/Nb = 97/3 | 94.8 | 20.2 | 78.8 | 0.5 | 0.5 | 99.0 | 33.2 |
| 12 | Fe/Ta = 97/3 | 90.1 | 15.9 | 82.4 | 0.3 | 1.4 | 98.3 | 37.4 |
| 13 | Fe/Ge = 97/3 | 100 | 0.7 | 98.6 | 0.3 | 0.4 | 99.3 | 31.4 |
| 14 | Fe/Ga = 97/3 | 100 | 4.7 | 94.1 | 0.4 | 0.8 | 98.8 | 30.7 |

Note:
The data goven in Table 2 were obtained at the end of 20 hours after the initiation of the reaction when the reaction was in the steady state.

EXAMPLES 15 TO 24

The same procedure as in Example 1 was repeated except that a mixture of methanol, phenol and H₂O in a mole ratio of 5:1:2 was used instead of the mixture of methanol and phenol, the temperature of reaction was changed to 355° C., and the reaction time was changed as shown in Table 3. The results are shown in Table 3.

Catalysts comprising components (A), (B) and (C) were prepared in the same way as in Example 25 except as noted in Table 4, and the reaction was carried out in the same way as in Example 25 under the conditions shown in Table 4. The results are also shown in Table 4.

The following compounds were used for forming the component (C).
Mg: magnesium nitrate
Zn: zinc nitrate

TABLE 3

| Example | Catalyst (metal atom ratio) | Conversion of phenol (%) | Selectivity for o-cresol (%) | Selectivity for 2,6-xylenol (%) | Selectivity for 2,4,6-trimethyl phenol (%) | Selectivity for others (%) | Selectivity for o-methylation (%) | Ratio of decomposition of methanol (%) |
|---|---|---|---|---|---|---|---|---|
| 15 | Fe/Ga = 98.2/1.8 | 100 | 3.8 | 93.7 | 1.0 | 1.5 | 97.5 | 32.8 |
| 16 | Fe/Ga = 98.2/1.8 | 96.8 | 28.4 | 70.0 | 0.6 | 1.0 | 98.4 | 33.1 |
| 17 | Fe/Ga = 98.2/1.8 | 100 | 3.0 | 95.5 | 0.4 | 1.1 | 98.5 | 31.2 |
| 18 | Fe/Ga = 98.2/1.8 | 96.2 | 25.3 | 73.8 | 0.1 | 0.8 | 99.1 | 30.0 |
| 19 | Fe/Ge = 98.2/1.8 | 100 | 2.9 | 95.0 | 0.9 | 1.2 | 97.9 | 29.0 |
| 20 | Fe/Ge = 98.2/1.8 | 97.2 | 21.1 | 77.3 | 0.6 | 1.0 | 98.4 | 30.0 |
| 21 | Fe/Ge = 98.2/1.8 | 100 | 1.2 | 97.0 | 1.1 | 0.7 | 98.2 | 29.4 |
| 22 | Fe/Ge = 98.2/1.8 | 98.8 | 15.9 | 82.7 | 0.8 | 0.6 | 98.6 | 30.6 |
| 23 | Fe/Ge = 98.1/1.9 | 100 | 2.4 | 96.1 | 1.2 | 0.3 | 98.5 | 29.2 |
| 24 | Fe/Ge = 98.1/1.9 | 98.7 | 17.7 | 80.8 | 0.7 | 0.8 | 98.5 | 30.5 |

EXAMPLE 25

Ferric nitrate nonahydrate (202.0 g) was dissolved in 2 liters of distilled water, and 25% ammonia water was gradually added to adjust the pH of the solution to 7. The resulting precipitate was washed with water, and Al: aluminum nitrate
Si: silica sol
Cr: chromium nitrate
Zr: zirconium nitrate Basic alkali metal compound: potassium carbonate potassium nitrate, sodium carbonate
Carbon: graphite
Sn: tin nitrate
Mo: ammonium molybdate
W: ammonium tungstate

TABLE 4

| Example | Catalyst (metal atom ratio) | Conversion of phenol (%) | Selectivity for o-cresol (%) | Selectivity for 2,6-xylenol (%) | Selectivity for 2,4,6-trimethyl phenol (%) | Selectivity for others (%) | Selectivity for o-methylation (%) | Ratio of decomposition of methanol (%) |
|---|---|---|---|---|---|---|---|---|
| 25 | Fe/Ge/Al = 97/1.8/1.2 | 100 | 3.0 | 95.3 | 1.4 | 0.3 | 98.3 | 28.1 |
| 26 | Fe/Ge/Al = 97/1.8/1.2 | 99.5 | 6.4 | 91.7 | 1.0 | 0.9 | 98.1 | 25.8 |
| 27 | Fe/Ga/Al = 97/1.8/1.2 | 100 | 6.1 | 91.6 | 1.8 | 0.5 | 97.7 | 32.9 |
| 28 | Fe/Ga/Al = 97/1.8/1.2 | 98.6 | 12.9 | 85.8 | 0.7 | 0.6 | 98.7 | 30.2 |
| 29 | Fe/Go/Cr = 97/1.8/1.2 | 99.7 | 5.1 | 93.6 | 0.6 | 0.7 | 98.7 | 34.8 |
| 30 | Fe/Go/Cr = 97/1.8/1.2 | 98.7 | 8.9 | 90.0 | 0.4 | 0.7 | 98.9 | 33.0 |
| 31 | Fe/Ga/Zr = 97/1.8/1.2 | 100 | 5.0 | 93.7 | 0.5 | 0.8 | 98.7 | 30.8 |
| 32 | Fe/Ga/Zr = 97/1.8/1.2 | 98.9 | 14.0 | 84.1 | 0.2 | 1.7 | 98.0 | 28.9 |
| 33 | Fe/Ga/K$_2$CO$_3$ = 98/1.9/0.1 | 100 | 5.1 | 93.6 | 0.6 | 0.7 | 98.7 | 30.9 |
| 34 | Fe/Ga/K$_2$CO$_3$ = 98/1.9/0.1 | 98.2 | 15.4 | 83.7 | 0.2 | 0.7 | 97.1 | 28.8 |
| 35 | Fe/Ge/Mg = 97/1.8/1.2 | 100 | 7.2 | 91.0 | 1.2 | 0.6 | 98.2 | 31.6 |
| 36 | Fe/Ge/Mg = 97/1.8/1.2 | 98.8 | 12.6 | 85.5 | 0.8 | 1.1 | 98.1 | 27.2 |
| 37 | Fe/Ge/Zn = 97/1.8/1.2 | 100 | 3.8 | 94.2 | 1.6 | 0.4 | 98.0 | 34.2 |
| 38 | Fe/Ge/Zn = 97/1.8/1.2 | 98.2 | 8.9 | 89.0 | 1.0 | 1.1 | 97.9 | 32.6 |
| 39 | Fe/Ge/C = 97/1.8/1.2 | 100 | 4.0 | 93.8 | 1.8 | 0.4 | 97.8 | 35.6 |
| 40 | Fe/Ge/C = 97/1.8/1.2 | 98.2 | 10.5 | 87.2 | 1.1 | 1.2 | 97.7 | 38.2 |
| 41 | Fe/Ge/Si = 97/1.8/1.2 | 100 | 5.0 | 92.8 | 1.3 | 0.9 | 98.4 | 35.0 |
| 42 | Fe/Ge/Si = 97/1.8/1.2 | 98.0 | 11.5 | 86.9 | 1.0 | 0.6 | 97.7 | 32.9 |
| 43 | Fe/Ge/Cr = 97/1.8/1.2 | 100 | 2.0 | 96.7 | 0.8 | 0.5 | 98.7 | 30.5 |
| 44 | Fe/Ge/Cr = 97/1.8/1.2 | 99.2 | 5.6 | 93.2 | 0.6 | 0.6 | 98.8 | 31.1 |
| 45 | Fe/Ge/Zr = 97/1.8/1.2 | 100 | 4.3 | 94.0 | 0.8 | 0.9 | 98.3 | 28.2 |
| 46 | Fe/Ge/Zr = 97/1.8/1.2 | 99.4 | 10.4 | 88.4 | 0.6 | 0.6 | 98.8 | 26.4 |
| 47 | Fe/Ge/Mo = 97/1.8/1.2 | 100 | 6.9 | 91.4 | 1.2 | 0.5 | 98.3 | 35.8 |
| 48 | Fe/Ge/Mo = 97/1.8/1.2 | 97.8 | 11.4 | 87.1 | 0.8 | 0.7 | 98.5 | 34.2 |
| 49 | Fe/Ge/Sn = 97/1.8/1.2 | 100 | 7.9 | 90.8 | 0.8 | 0.5 | 98.7 | 34.9 |
| 50 | Fe/Ge/Sn = 97/1.8/1.2 | 97.6 | 12.8 | 86.0 | 0.4 | 0.8 | 98.8 | 35.1 |
| 51 | Fe/Ge/W = 97/1.8/1.2 | 100 | 7.7 | 91.0 | 1.1 | 0.2 | 98.7 | 34.8 |
| 52 | Fe/Ge/W = 97/1.8/1.2 | 98.0 | 11.4 | 87.0 | 0.7 | 0.9 | 98.4 | 33.9 |
| 53 | Fe/Ge/K$_2$CO$_3$ = 98/1.9/0.1 | 100 | 3.8 | 94.8 | 0.7 | 0.7 | 98.6 | 29.4 |
| 54 | Fe/Ge/K$_2$CO$_3$ = 98/1.9/0.1 | 99.8 | 10.4 | 87.8 | 0.5 | 1.3 | 98.2 | 27.8 |
| 55 | Fe/Ge/K$_2$O = 98/1.9/0.1 | 100 | 4.1 | 94.2 | 0.5 | 1.2 | 98.3 | 28.4 |
| 56 | Fe/Ge/K$_2$O = 98/1.9/0.1 | 99.0 | 13.5 | 85.0 | 0.4 | 1.1 | 98.5 | 27.1 |
| 57 | Fe/Ge/Na$_2$CO$_3$ = 98/1.9/0.1 | 100 | 5.4 | 93.8 | 0.2 | 0.6 | 99.2 | 28.0 |
| 58 | Fe/Ge/Na$_2$CO$_3$ = 98/1.9/0.1 | 98.6 | 14.0 | 84.9 | 0.1 | 1.0 | 98.9 | 28.2 |
| 59 | Fe/Hf/Al = 97/1.8/1.2 | 100 | 6.8 | 91.9 | 1.5 | 0.6 | 97.9 | 33.6 |
| 60 | Fe/Hf/Al = 97/1.8/1.2 | 98.4 | 13.1 | 85.2 | 0.9 | 0.8 | 98.3 | 34.2 |
| 61 | Fe/Hf/Cr = 97/1.8/1.2 | 100 | 2.4 | 96.0 | 1.0 | 0.6 | 98.4 | 32.0 |
| 62 | Fe/Hf/Cr = 97/1.8/1.2 | 99.4 | 2.9 | 95.1 | 0.7 | 1.3 | 98.0 | 31.4 |
| 63 | Fe/Hf/K$_2$CO$_3$ = 98/1.9/0.1 | 99.2 | 8.0 | 90.6 | 0.6 | 0.8 | 98.6 | 32.2 |
| 64 | Fe/Hf/K$_2$CO$_3$ = 98/1.9/0.1 | 96.0 | 18.7 | 80.0 | 0.3 | 1.0 | 98.7 | 31.6 |
| 65 | Fe/Ta/Al = 97/1.8/1.2 | 97.2 | 9.9 | 89.0 | 0.6 | 0.5 | 98.9 | 36.8 |
| 66 | Fe/Ta/Al = 97/1.8/1.2 | 96.1 | 14.7 | 83.6 | 0.3 | 1.4 | 98.3 | 35.6 |
| 67 | Fe/Ta/Cr = 97/1.8/1.2 | 98.9 | 8.8 | 90.2 | 0.6 | 0.4 | 99.0 | 36.2 |
| 68 | Fe/Ta/Cr = 97/1.8/1.2 | 97.3 | 12.2 | 86.6 | 0.3 | 0.9 | 98.9 | 34.0 |

What we claim is:

1. In a process for producing a mono- or di-orthomethyl-substituted phenol which comprises methylating a phenol having the following formula

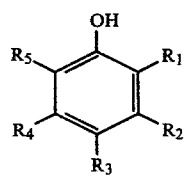

wherein each of R$_1$, R$_2$, R$_3$, R$_4$ and R$_5$ represents a member selected from the group consisting of hydrogen, lower alkyl, cyclohexyl and phenyl, provided that one or both R$_1$ and R$_5$ are hydrogen atoms, with methanol, in a vapor phase reaction at a temperature of about 250° to about 450° C. and a pressure of about 1 to about 30 kg/cm$^2$-gauge, in the presence of a catalytic amount of a catalyst comprising (A) a major proportion of an oxide of iron and (B) a minor proportion of at least one oxide of a metal other than iron, the improvement wherein said metal other than iron in component (B) is a metal selected from the group consisting of Ga, Ge, Y, Nb, Hf, Bi and Ta, and the amount of component (B) is about 0.003 to about 0.3 gram-atom, as metal, per gram-atom of iron.

2. The process of claim 1 wherein said catalyst further comprises, as a third component (C), at least one compound selected from the group consisting of (C-1) an oxide of a metal selected from the group consisting of Mg, Zn, Al, Si, Cr, Sn, Mo, W and Zr, (C-2) a basic alkali metal compound of a metal selected from K, Na and Li, and (C-3) carbon.

3. The process of claim 1 wherein the amount of the second component (B) of the catalyst is about 0.005 to about 0.15 gram-atom, as metal, per gram-atom of iron.

4. The process of claim 2 wherein the amount of the third component (C) of the catalyst is about 0.0001 to about 0.1 gram-atom, as metal or carbon, per gram-atom of iron.

5. The process of claim 1 wherein the catalytic methylation is carried out in the vapor phase at a LHSV of 0.1 to 10 hr$^{-1}$.

* * * * *